United States Patent
Van Netten

(10) Patent No.: US 6,945,127 B2
(45) Date of Patent: Sep. 20, 2005

(54) PERSONAL AND ENVIRONMENTAL AIR SAMPLING APPARATUS

(76) Inventor: Christiaan Van Netten, RR #7, 11666 Wilson Street, BC, Mission (CA), V4S 1B6

( * ) Notice: Subject to any disclaimer, the term of this patent is extended or adjusted under 35 U.S.C. 154(b) by 30 days.

(21) Appl. No.: 10/398,763

(22) PCT Filed: Oct. 5, 2001

(86) PCT No.: PCT/CA01/01391
§ 371 (c)(1),
(2), (4) Date: Sep. 15, 2003

(87) PCT Pub. No.: WO02/31468

PCT Pub. Date: Apr. 18, 2002

(65) Prior Publication Data

US 2004/0045376 A1 Mar. 11, 2004

Related U.S. Application Data

(60) Provisional application No. 60/239,813, filed on Oct. 11, 2000.

(51) Int. Cl.$^7$ .................................................. G01N 1/00
(52) U.S. Cl. .................................................. 73/863.23
(58) Field of Search .................. 73/863.01, 863.21, 73/863.22, 863.23, 863.24, 863.25, 31.01, 31.02, 28.01, 28.04, 28.05; 96/115, 413

(56) References Cited

U.S. PATENT DOCUMENTS 4,080,832 A    3/1978  Moody et al.
4,432,248 A    2/1984  Lalin
4,616,513 A   10/1986  Gibson et al.
5,018,395 A    5/1991  Hickox et al.
6,085,601 A *  7/2000  Linker et al. ............ 73/863.12
6,267,016 B1   7/2001  Call et al.

FOREIGN PATENT DOCUMENTS

DE    88 12 640 U    3/1989
EP    0 373 045 A    6/1990
GB    1 165 769     10/1969
WO    WO 90/10282    9/1990
WO    WO 02/31468    4/2002

* cited by examiner

Primary Examiner—Robert Raevis
(74) Attorney, Agent, or Firm—Berenato, White & Stavish, LLC

(57) ABSTRACT

A self sealing air sampling apparatus includes a body with a filter therein and an air moving device, such as a fan, mounted therein for moving air through the filter. There is an air inlet communicating with the filter. There is also a air outlet communicating with the filter. A manually operable control simultaneously opens the air inlet and the air outlet and operates the air moving device for moving air from the air inlet, through the filter and out through the air outlet. For example, the body may be cylindrical and have a cylindrical shell rotatably mounted thereon. The shell and the body have air inlet openings and air outlet openings which are aligned when the shell is rotated in one direction and become unaligned when the shell is rotated in an opposite direction thus sealing off the filter compartment from the outside environment. Rotation of the shell also closes a switch to operate the fan when the shell is rotated in the one direction.

15 Claims, 6 Drawing Sheets

PERSONAL AND ENVIRONMENTAL AIR SAMPLING APPARATUS

This application claims the benefit of the Provisional application Ser. No. 60/239,813, filed Oct. 11, 2000.

BACKGROUND OF THE INVENTION

This invention relates to air sampling devices and, in particular, to personal sampling devices easily operable by untrained people.

Flight crews and aircraft passengers are occasionally exposed to unfavorable air quality conditions. These conditions typically occur during 1 out of 1000 flight segments, depending upon the airline and the maintenance of the aircraft. A large majority of these incidents are caused by contamination of the aircraft air from hydraulic fluid which leaks into the air intake of the Auxiliary Power Unit (APU) or from oil seal leakage into the compressor stages of the jet engines which are used to pressurize the aircraft and to provide the aircraft with fresh air.

Bleed air from these engines is exposed to elevated temperatures, often in excess of 500 degrees C. Any oil or hydraulic fluid contaminant in this air will pyrolize, volatize, or both. This often results in flight crews and passengers being exposed to smoke in the cabin. Acute and long-term symptoms experienced by flight crews during these incidents are consistent with exposures to the agents associated with oil and hydraulic fluid constituents.

It is difficult however to measure exposure levels during these incidents because of their sporadic nature. This makes it virtually impossible to have trained individuals, and specialized equipment, in aircraft when such incidents occur. The equipment previously available is expensive and difficult to operate for the average flight attendant or other member of the flight crew. Accordingly, very little exposure data is available.

Some of these incidents have resulted in near fatal accidents, i.e., both pilots becoming incapacitated, as well as disabling flight attendants and pilots on a long-term basis. It is therefore critical to provide a practical means of measuring the exposures of flight crews and passengers when such events occur. The derived information can be used to provide a basis for medical treatment as well to prevent future incidence of such exposure to contaminants.

Accordingly it is an object of the invention to provide an improved air sampling apparatus which is inexpensive enough so that each individual crew member or aircraft can be provided with the apparatus on a routine basis.

It is also an object of the invention to provide an improved air sampling apparatus which is simple to operate so that a flight attendant or other member of a flight crew can easily operate the apparatus with minimal training or instructions.

Is a further object of the invention to provide an improved personal and environmental air sampling apparatus which is compact so that it does not occupy an inordinate amount of the limited space and can be carried in a purse or pocket.

It is a still further object of the invention to provide an improved air sampling apparatus which is rugged in construction and reliable in operation so that it will operate reliably without requiring delicate handling

SUMMARY OF THE INVENTION

In accordance with these objects, there is provided an air sampling apparatus which includes a body having a filter mounted therein and an air moving device mounted therein for moving air through the filter. There is an air inlet communicating with the filter. An air outlet also communicates with the filter. There is a manually operable control which simultaneously opens the air inlet and the air outlet and operates the air moving device for moving air from the air inlet, through the filter and out through the air outlet. Preferably the control can simultaneously close the air inlet and the air outlet and render the air moving device inoperative.

The control may include an outer member movably mounted on the body. The air inlet includes at least one air inlet opening on the body and at least one air inlet opening on the outer member. The air outlet includes at least one air outlet opening on the body and at least one air outlet opening on the outer member. Said at least one air inlet opening on the body is aligned with said at least one air inlet opening on the outer member. Said at least one air outlet opening on the body is aligned with said at least one air outlet opening on the outer member when the outer member is moved in a first direction, to move air through the filter. Preferably said at least one air inlet opening on the body becomes unaligned with said at least one air outlet opening on the outer member and said at least one air outlet opening on the body becomes unaligned with said at least one air outlet opening on the outer member, when the outer member is moved in a second direction, to seal the apparatus.

The control may include a switch mounted on the body which is contacted by the outer member, to close the switch and operate the air moving device when the outer member is moved in the first direction, and to open the switch and stop the air moving device when the outer member is moved in the second direction.

The outer member may be rotatably mounted on the body. The first direction is then a first rotational direction and the second direction is then a second rotational direction which is opposite the first direction. For example, the body may be generally cylindrical and the outer member may be a cylindrical shell mounted on the body.

An air sampling apparatus according to the invention offers distinct advantages compared to the prior art. The apparatus can be operated by simply moving a manually operable control and this simultaneously opens the air inlet and air outlet and operates the fan or other air moving device which moves air through the filter. For example, this may simply be accomplished by rotating a cylindrical shell mounted on a cylindrical body containing the principal components. When the sampling process is completed, another movement of the manually operable control stops the air moving device and seals the openings. This is simply accomplished by rotating the shell in the opposite direction for this preferred embodiment.

When the sample has been taken, the unit is economical enough to be sent to a laboratory in its entirety for analysis. There is no need for the flight crew or other user to remove and store filters which would necessitate disassembly of the apparatus and potential contamination of the filter.

In brief, the apparatus can be easily operated by most people without any training at all and with simple instructions which can accompany the unit. Also the unit is simple and inexpensive enough so all aircraft can carry such an apparatus for the relatively remote possibility that air contamination will occur during any particular flight.

DETAILED DESCRIPTION OF THE PREFERRED EMBODIMENTS

Figure 1:
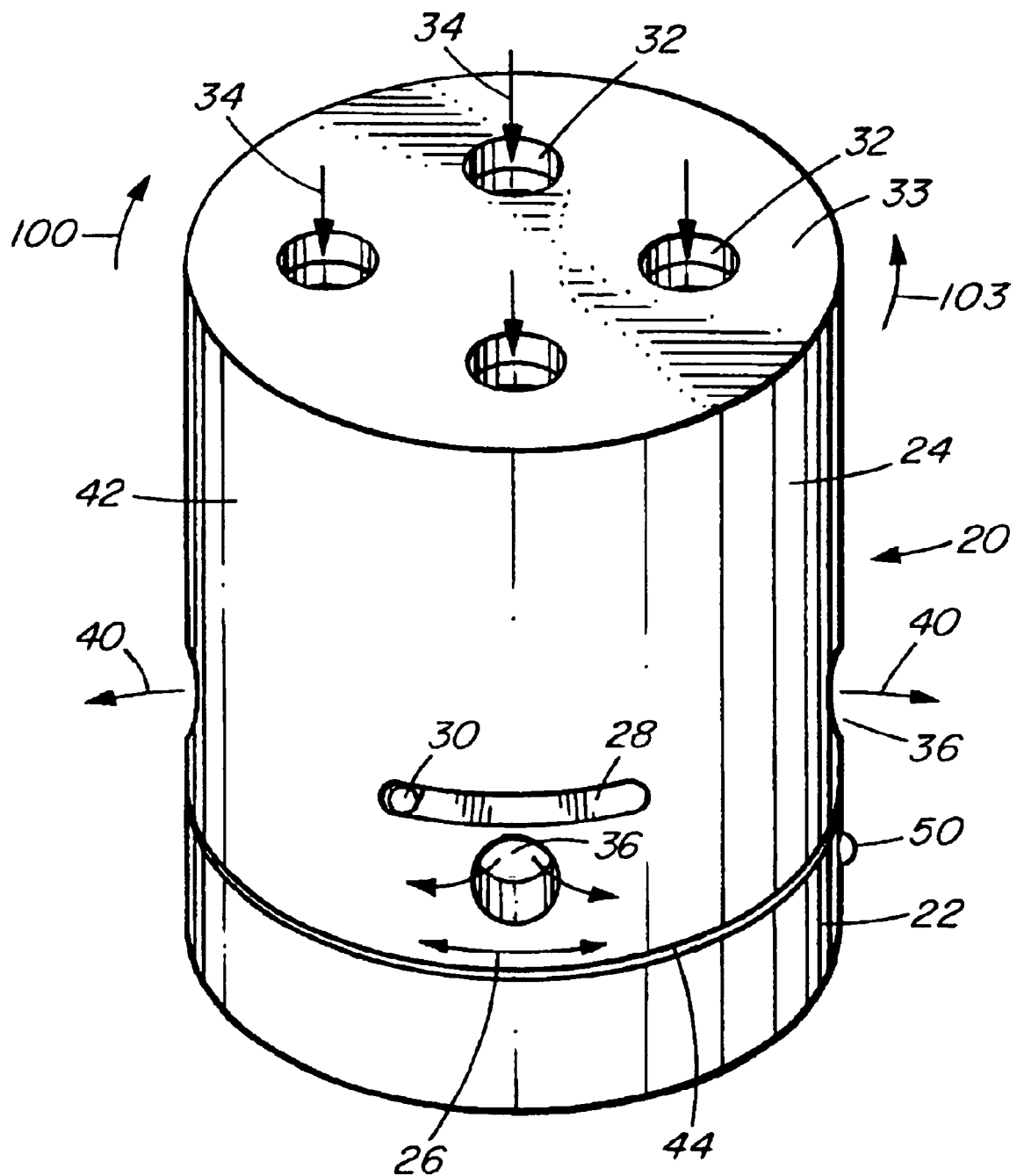
FIG. 1 is an isometric view of an air sampling apparatus according to an embodiment of the invention.

Referring to the drawings, and first to FIG. 1, this shows an air sampling apparatus 20 suitable for sampling air in aircraft or other locations where contaminants may occur. The apparatus in this example includes a cylindrical body 22 which has a cylindrical outer shell 24 mounted thereon for rotation in the directions indicated by arrows 26. The shell tightly engages the body for a sealing fit, apart from the openings described below. There is a slot 28 in the shell and a screw 30 extending through the slot into the body which limit the amount of rotational movement of the shell on the body. The apparatus of this example fits within a cylinder 2.5 inches in diameter and 3 inches long although the size may vary in other embodiments.

The shell has four air inlet openings 32 in top 33 of the shell to admit air into the apparatus as indicated by arrows 34. The number, size and positioning of the openings can vary in alternative embodiments. The shell also has four air outlet openings 36 for air exiting the apparatus as indicated by arrows 40 (only three being visible in FIG. 1). In this example the openings are in cylindrical side 42 of the shell near its bottom 44 and are 90 degrees apart. In alternative embodiments the number and positions of the openings can change. There is also an LED 50 which lights to indicate that the apparatus is operational.

Figure 2:
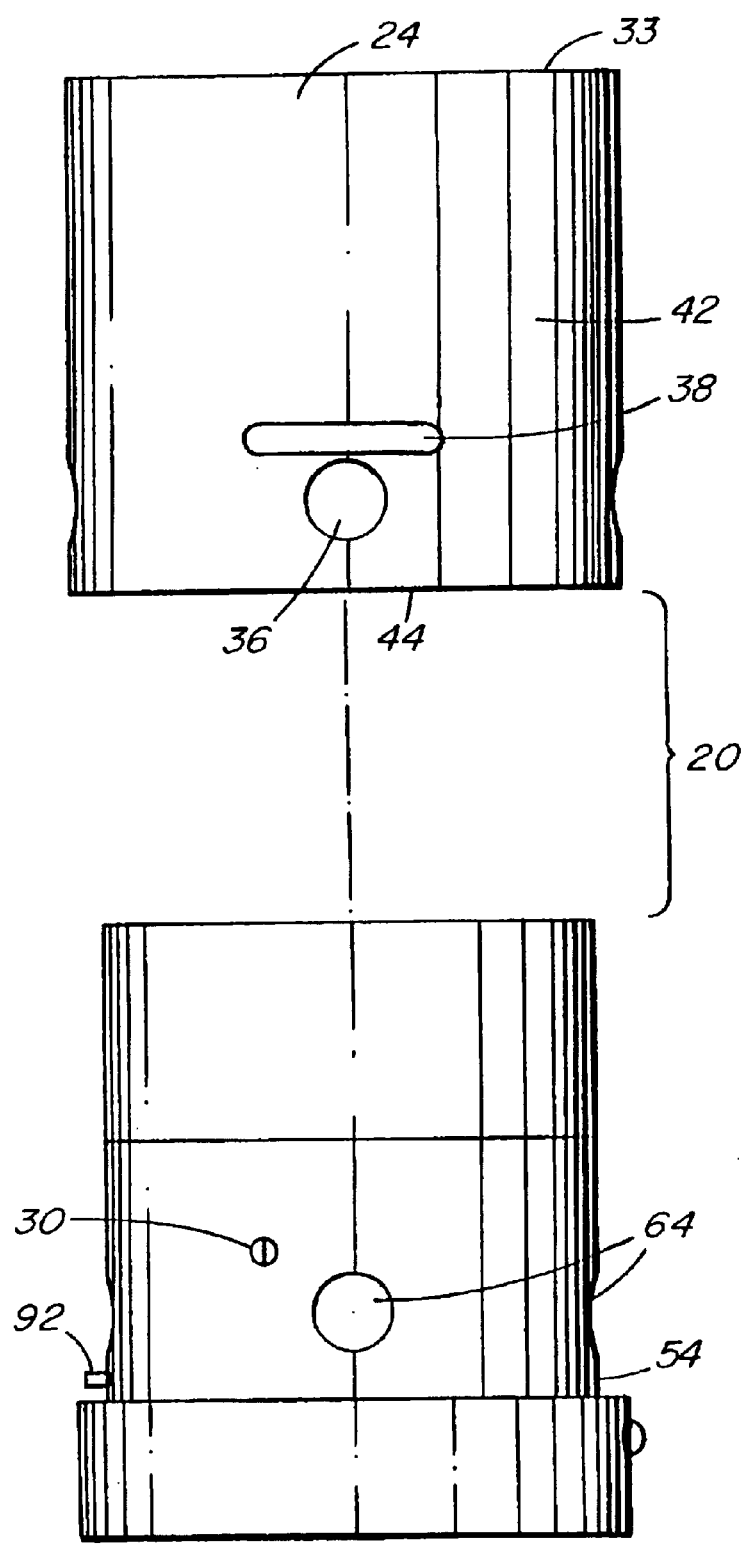
FIG. 2 is a simplified, exploded side view thereof.
Figure 3:
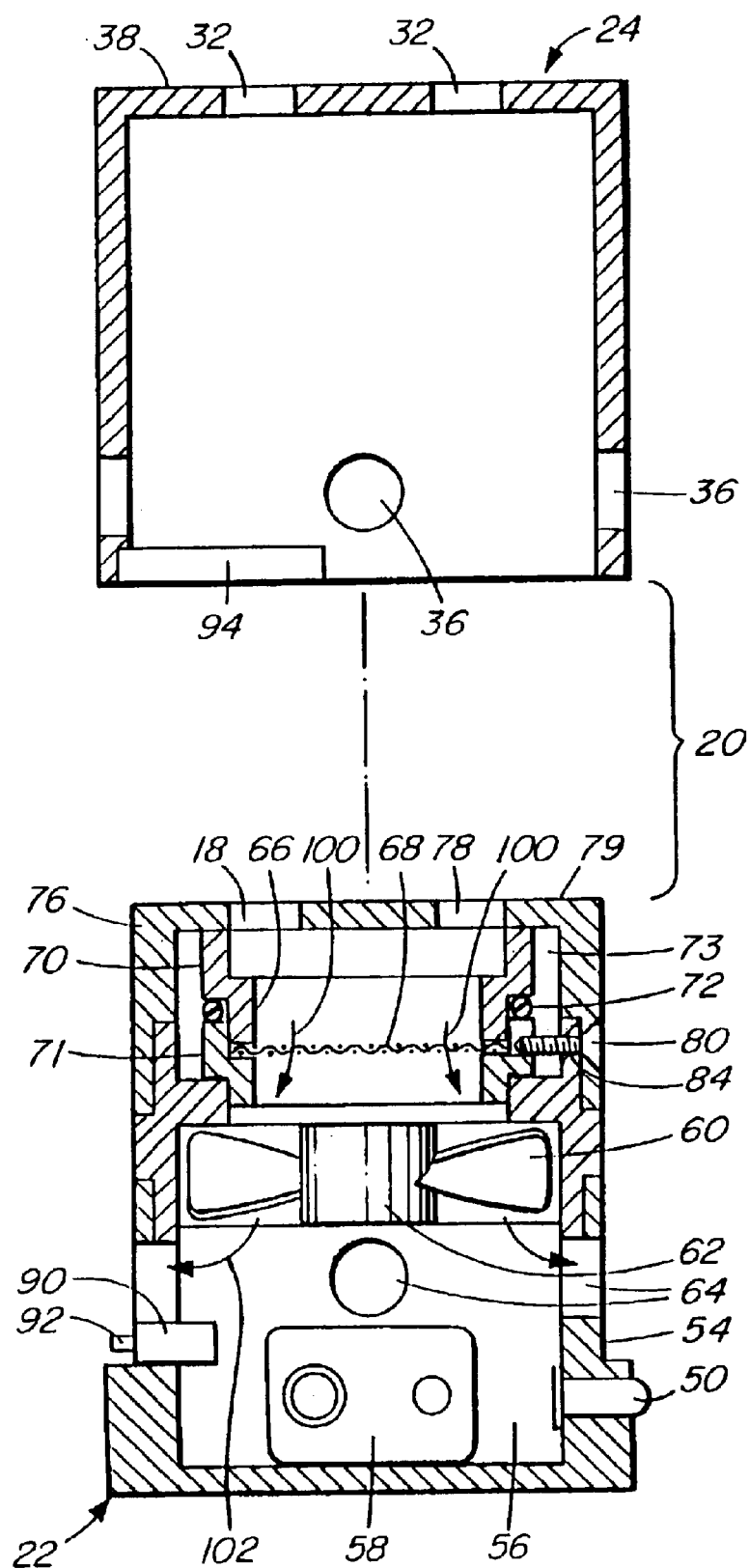
FIG. 3 is a simplified, diametrical section of the embodiment of FIGS. 1 and 2.

The body 22 has a lower portion which comprises fan housing 54 shown in FIGS. 2 and 3. The fan housing includes a chamber 56 which contains a battery 58, a 9 volt battery in this example, and a fan 60 mounted above the battery. This particular fan is an axial flow fan powered by a motor 62 connected to the battery 58. There is a series of four air outlet openings 64 extending about the fan housing and spaced-apart 90 degrees (only three being visible in FIG. 3). These correspond in number and position to the air outlet openings 36 in the shell. Openings 64, together with openings 36, comprise air outlets for the apparatus.

Figure 4:
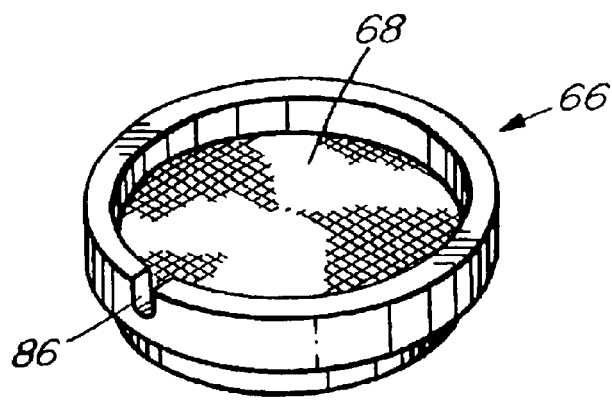
FIG. 4 is an isometric view of the lower portion of the filter cassette thereof.
Figure 6:
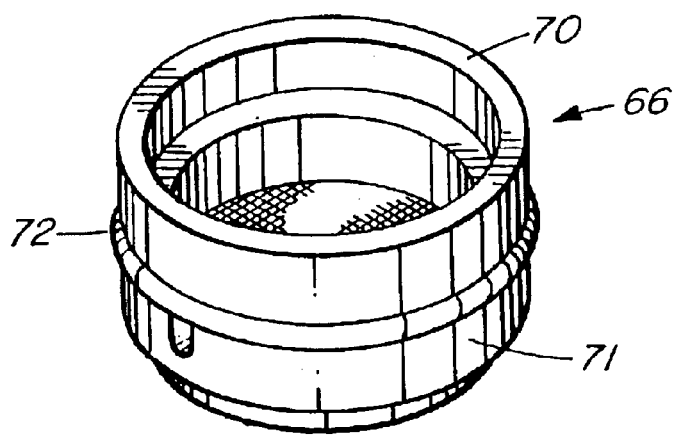
FIG. 6 is a reduced isometric view of the filter cassette thereof.

There is a standard 37 mm filter cassette 66 mounted above the fan in filter compartment 73 and which contains a filter disk 68 as shown in FIG. 4. Other types of filters or size of filter cassette holders could be used in other embodiments. There is an upper filter housing 70 mounted on lower filter housing 71 of the filter cassette with an O-ring 72 compressed therebetween as seen best in FIG. 6.

Figure 5:
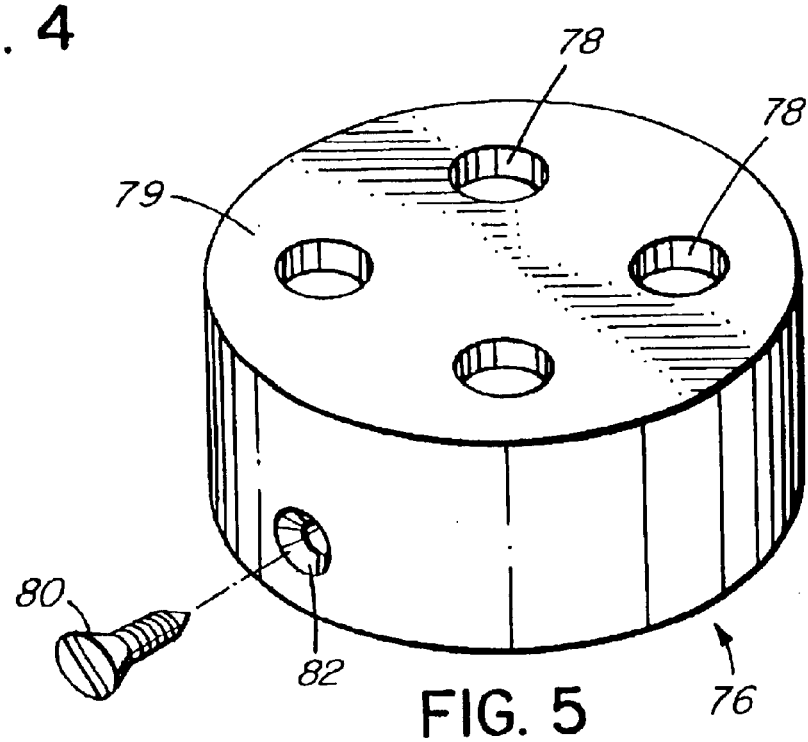
FIG. 5 is an isometric view of the air inlet housing of the body thereof.

The body has an air inlet housing 76, shown best in FIG. 5, mounted on top of the filter housing. The air inlet housing has four air inlet openings 78 in top 79 thereof, which correspond in position and number to the air inlet openings 32 in shell 24. The openings 78 and openings 32 together comprise air inlets for the apparatus. A screw 80 extends through opening 82 in the air inlet housing, through opening 84 in the fan housing and engages notch 86 on the filter cassette 66.

There is a switch 90 mounted on the fan housing which has a button 92. The button engages a ramp 94, on the inside of the shell 24, shown only in FIG. 3, whereby the button is depressed to close the switch when the shell is rotated in one direction and is released, to open the switch, when the shell is rotated in the opposite direction. The switch is operatively disposed between the fan motor and the battery and thus controls operation of the fan.

In operation, with reference to FIG. 1, the air sampling apparatus is operated by rotating the shell 24 in one rotational direction, for example clockwise as shown by arrow 100, the figure showing the shell partially rotated. A 45 degree twist is used in this example although this could vary in other embodiments. This twist causes the air inlet openings 32 on the shell to align with the air inlet openings 78 on the body to admit air into the apparatus. At the same time, the air outlet openings 36 of the shell align with air outlet openings 64 in the body to permit air to exit the apparatus. Simultaneously, the rotation causes ramp 94 on the inside of the shell to depressed button 92 and close switch 90. This operates the air moving device, in the form of fan 60, by means of battery 58 powering motor 62.

The apparatus is operated for a preset period of time. The air enters the apparatus as indicated by arrows 34 in Figure to cause suction of fan 60 as indicated by arrows 100 in FIG. 3. This draws air through the filter 68. Air expelled, by the fan exits the apparatus through the outlet openings 64 in the body, as shown by arrows 102 in FIG. 3. In this example the air flow is between 0.5 and 1.0 liters per minute and the device can operate from 2–5 hours, depending upon the filter used. The device however can be scaled upward to use a larger fan, larger battery and larger filters, or scaled downward, for different air quality applications. In addition, the filter compartment can also be used to incorporate other air contaminant capturing agents such as adsorbents and adsorbents to target specific contaminants.

After the apparatus has been operated for the preset time, the user rotates shell 24 in the opposite direction, counter-clockwise in this particular embodiment, as illustrated by arrow 103 in FIG. 1. This causes the air inlet openings 32 in the shell to become unaligned with air inlet openings 73 in the body. Simultaneously the air outlet openings 36 in the shell become maligned with air outlet openings 604 in the body. Thus the inside of the apparatus, including the filter, are effectively sealed. At the same time, ramp 94 backs off of button 92 which causes the switch 92 to open and stops the fan motor 62. The unit can then be placed in a suitable storage position and forwarded to a laboratory for analysis at a convenient time.

Figure 7:
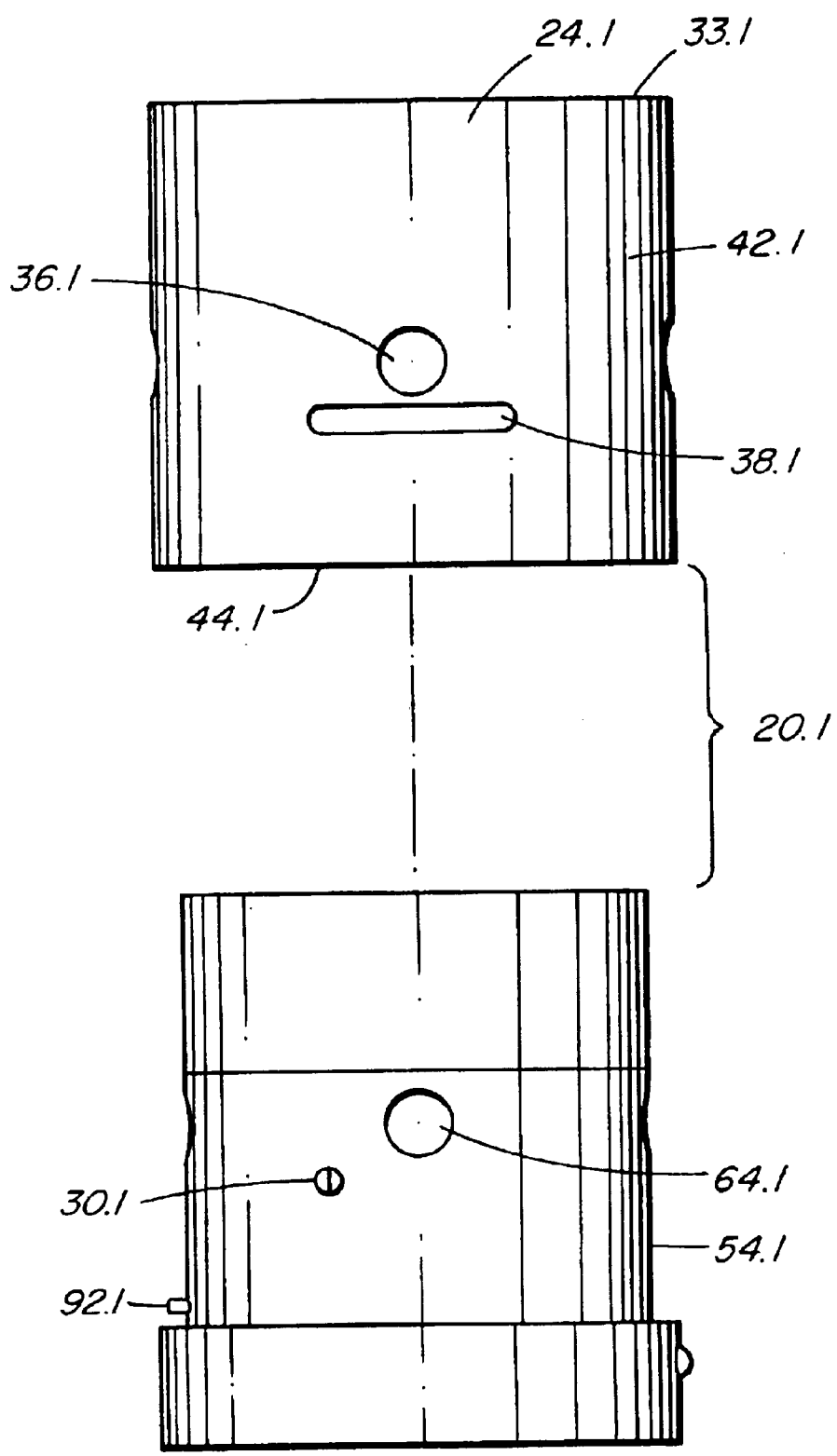
FIG. 7 is a view similar to FIG. 1 of an alternative embodiment with a centrifugal fan.
Figure 8:
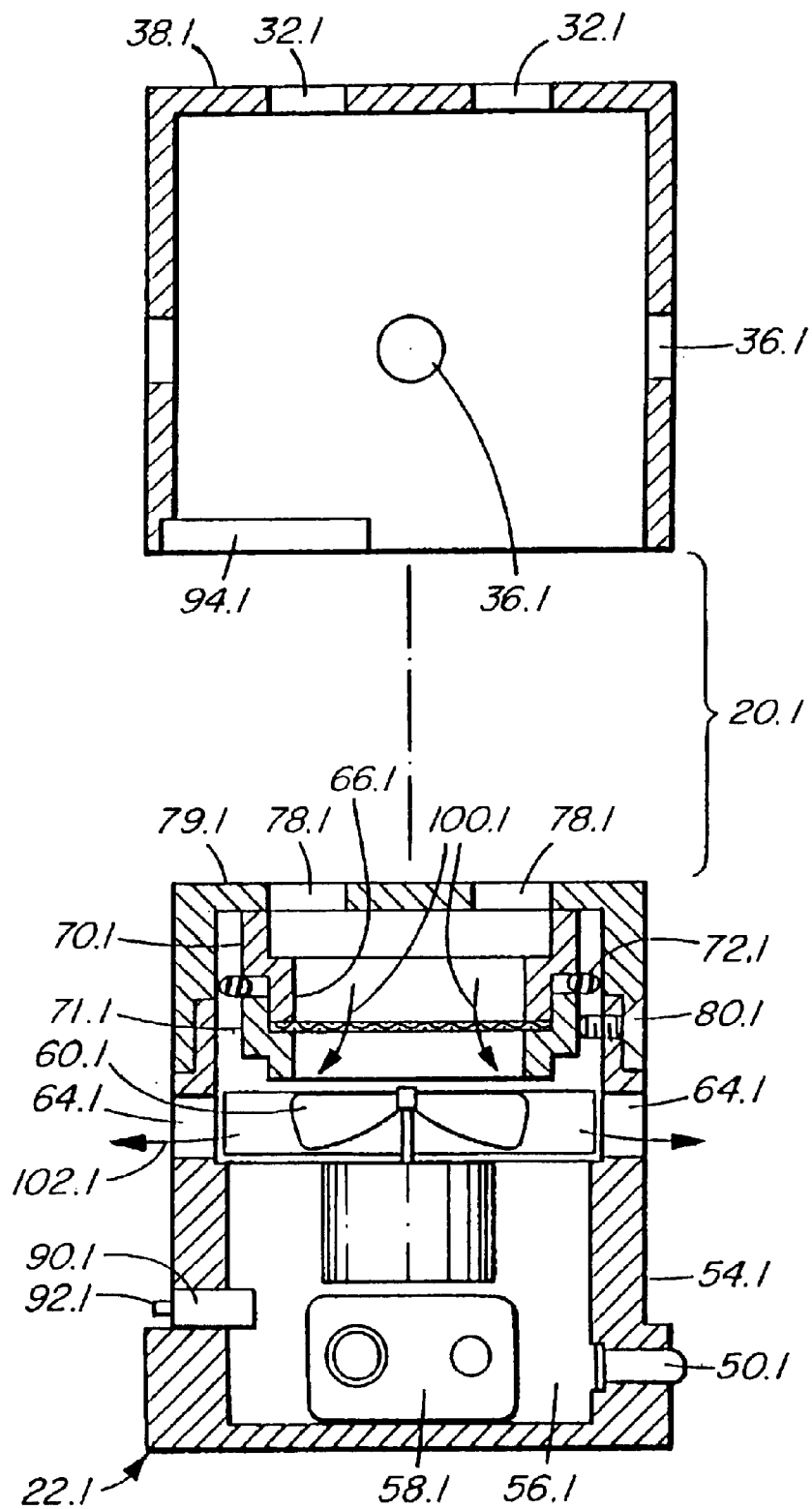
FIG. 8 is a view similar to FIG. 2 showing the embodiment of FIG. 7.

A centrifugal fan 60.1 shown in FIGS. 7 and 8, can be substituted in alternative embodiment for the axial fan 60 shown in FIG. 3. In this embodiment where like parts have like numbers as in the previous embodiment, with the additional designation "0.1", the air outlet openings 64.1 are moved upwardly to be in alignment with the fan instead of being below the fan as is the case with the axial fan of the previous embodiment. Likewise outlet openings 36.1 in shell 24.1 are corresponding raised.

It will be understood by someone skilled in the art that many of the details provided above are by way of example only and are not intended to limit the scope of the invention which is to be interpreted with reference to the following claims.

What is claimed is:

1. An air sampling apparatus, comprising:
   a body having a filter mounted therein and an air moving device mounted therein for moving air through the filter;

an air inlet communicating with the filter, an air outlet communicating with the filter; and a manually operable control which simultaneously opens the air inlet and the air outlet and operates the air moving device for moving air from the air inlet, through the filter and out through the air outlet, and wherein the control can simultaneously close the inlet and the outlet and render the air moving device inoperative.

2. The air sampling apparatus as claimed in claim 1, wherein the filter is sealed within the body when the air inlet and air outlet are closed.

3. The apparatus as claimed in claim 2, wherein the body is unsealed, and the apparatus activated when the control opens the air inlet and the air outlet.

4. The air sampling apparatus as claimed in claim 1, the control including an outer member movably mounted on the body, the air inlet including at least one air inlet opening on the body and at least one air inlet opening on the outer member, the air outlet including at least one air outlet opening on the body and at least one air outlet opening on the outer member, said at least one air inlet opening on the body being aligned with said at least one air inlet opening on the outer member and said at least one air outlet opening on the body being aligned with said at least one air outlet opening on the outer member when the outer member is moved in a first direction, to move air through the filter.

5. The air sampling apparatus as claimed in claim 4, wherein said at least one air inlet opening on the body becomes unaligned with said at least one air inlet opening on the outer member and said at least one air outlet opening on the body becomes unaligned with said at least one air outlet opening on the outer member, when the outer member is moved in a second direction, to seal the apparatus.

6. The apparatus as claimed in claim 5, wherein the control includes a switch mounted on the body which is contacted by the outer member, to close the switch and operate the air moving device when the outer member is moved in the first direction, and to open the switch and stop the air moving device when the outer member is moved in the second direction.

7. The apparatus as claimed in claim 6, wherein the outer member is rotatably mounted on the body, the first direction being a first rotational direction and the second direction being a second rotational direction which is opposite the first rotational direction.

8. The apparatus as claimed in claim 7, wherein the body is generally cylindrical and the outer member is a cylindrical shell rotatably mounted on the body.

9. The apparatus as claimed in claim 8, wherein the body and the outer member each has a top and a cylindrical side, said at least one air inlet opening on the body comprising an opening in the top of the body, said at least one air inlet opening on the outer member comprising an opening in the top of the outer member, said at least one air outlet opening on the body comprising an opening on the side of the body, and said at least one air outlet opening on the outer member comprising an opening on the side of the outer member.

10. The apparatus as claimed in claim 9, wherein the outer member has a ramp facing the switch on the body, the ramp closing the switch when the outer member is rotated in the first rotational direction and opening the switch when the outer-member is rotated in the second rotational direction.

11. The apparatus as claimed in claim 1, wherein the air moving device is a fan.

12. The apparatus as claimed in claim 11, wherein the fan is power operated.

13. The apparatus as claimed in claim 12, including a battery mounted in the body and connected to the fan.

14. The apparatus as claimed in claim 13, wherein the fan is an axial fan.

15. The apparatus as claimed in claim 13, wherein the fan is a centrifugal fan.

\* \* \* \* \*